March 9, 1948. H. C. SWIM Plant Pat. 787
NECTARINE PLANT
Filed Dec. 30, 1946
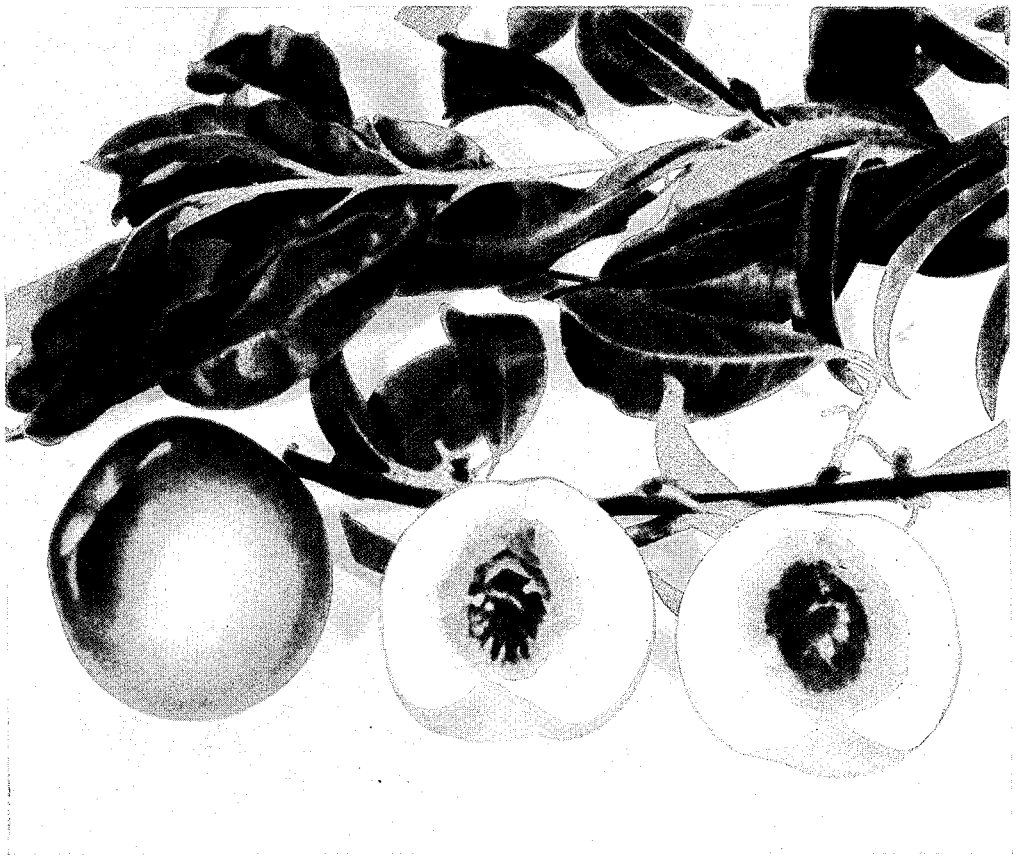
Inventor
H. C. Swim
By Robb & Robb
Attorneys Patented Mar. 9, 1948

Plant Pat. 787

UNITED STATES PATENT OFFICE

787

NECTARINE PLANT

Herbert C. Swim, Ontario, Calif., assignor to Armstrong Nurseries, Inc., Ontario, Calif., a corporation of California Application December 30, 1946, Serial No. 719,183

1 Claim. (Cl. 47—62)

The present invention relates to a new and distinct variety of nectarine plant originated from seed resulting from hand pollination of a seedling of "Goldmine" nectarine × "Rio Oso Gem" peach (Plant Patent 84) with pollen of a brother seedling of the same cross.

In points of novelty and distinctiveness, the above noted breeding has produced a fruit tree, the characteristics of which are unlike any other known variety of nectarine in commerce today, and the combination of these characteristics makes this new nectarine (both the tree and its fruit) stand out from all others in important respects, now to be specifically set forth.

(1) The flesh of this nectarine is yellow with much red coloring in the flesh and about the pit, the skin being more intensely colored with red pigment, as hereinafter noted, than other varieties of yellow-fleshed nectarines now available to commerce. This high color characteristically covers almost the entire surface of the fruit, but with occasional yellow or orange hues noticeable in the stem cavity.

(2) The flavor of the fruit is extraordinarily rich compared with nectarine varieties now in commerce. This flavor is mildly austere and very distinctive.

(3) So far as I am aware, this new variety has a greater resistance to delayed dormancy than other varieties now known to commerce, the index for winter chilling requirement being about like that of the peach variety known as "Redwing" (Pl. Pat. #621). Because of this resistance to delayed dormancy, this new variety is more productive in Southern California than other varieties now available.

(4) Another of its important characteristics is its early blooming date in Southern California, compared with other available varieties grown under comparable conditions, and the showy character of the blooms in mass, when the tree is at the peak of bloom, such showiness resulting from not only the large quantity of flowers, but also their large size, as well.

(5) Lastly, the fruit has a relatively thin skin, sufficiently crisp to be eaten with ease, thus making the new variety suitable only for home planting or for local market use, but adding to its desirability for these purposes. Furthermore, the skin has less tendency to crack than most varieties, being about like Lippiatt's Late Orange in this respect.

Asexual reproduction shows that these characteristics hold true through succeeding propagations.

In the drawing there are illustrated specimens of this new nectarine tree foliage and fruit, the latter being shown in elevation and in section, with and without the pit.

The following is a detailed description of the new variety based upon observations of specimens grown at Ontario, California, color terminology being in accord with Ridgway's Color Standard as regards the colors in the green and brown range, all other colors being in accordance with Robert F. Wilson's Horticultural Colour Charts:

Dates of first and last picking—varying somewhat from year to year because of variable winter chilling in Southern California, but usually ripens the last week in July or first week in August.

Tree: Large to medium; vigorous to medium; upright; spreading; vase formed; productive; regular bearer; hardiness untested.

*Trunk.*—Medium stocky; medium smooth.

*Branches.*—Medium stocky; medium smooth; dull; near Saccardo's Umber, Plate XXIX (Ridgway) on 2-year-old branch 1 cm. in diameter. *Lenticels*—medium number; medium size.

*Leaves.*—Length—10 to 15 cm. Width—3 to 4 cm. Large to medium; acuminate; linear lanceolate; acuminately pointed; thick to medium. *Color*—upper side of mature leaf near Cress Green, Plate XXXI (Ridgway); under side of mature leaf slightly darker than Asphodel Green, Plate XLI (Ridgway); midrib, near Chrysolite Green, Plate XXXI (Ridgway). *Smooth*—class 3, wavy and crinkled; see Blake, M. A. and E. M. Meader, Identification of Peach Varieties, Proc. Am. Soc. Hort. Sci., Vol. 37, pp. 203-206, 1939. *Margin* — crenate. *Petiole*—medium length, ½ to 1 cm. in length; medium thick. *Glands*—average number, four. Some opposite, others alternate or variable; large; reniform. Color, near Chrysolite Green, Plate XXXI (Ridgway). Position, near base of leaf on upper half of petiole; occasionally on the base of leaf blade. *Stipules*—early deciduous; 1 to 1⅛ cm. in length; very narrow with apex pointed; base approximately 1 mm. in width; irregular long glandular teeth on the margins.

*Flowers.*—Dates first and full bloom: first bloom—from March 6th to March 14th; full bloom—from March 18th to March 30th. Early compared with other standard varieties. *Size*—Large. *Color*—Pink, with reddish center.

Fruit:

*Maturity when described.*—Eating firm ripe July 30th.

*Size.*—Slightly variable; average medium. Diameter axial—2–2¼ inches. Transverse in suture plane—2–2⅛ inches. At right angles to suture plane—2–2¼ inches.

*Form.* — Slightly variable; symmetrical; broadly ovoid; cheeks rounded. *Suture*—Distinct; medium depth; extends from base to beyond apex; has slight marked depression beyond pistil point. *Ventral surface*—rounded slightly throughout both sides; lips—equal. *Cavity*—rounded with suture showing on one side. Depth, ¼ inch. Breadth, ¾ inch. Markings—a sharp deep suture in stem cavity. *Base*—rounded to truncate. *Apex*—depressed. Pistil point—depressed. *Stem*—Length, ¼ inch; medium to stout; glabrous. Adherence to stone—strong to medium.

*Skin.*—Medium thin; medium tender; tenacious to flesh. *Tendency to crack*—none. *Color*—near Chrysanthemum Crimson, Plate 824/1, page 169, varying somewhat depending on the amount of exposure to sun to near Blood Red, Plate 820/1, page 166. Base of most fruits, near Yellow Ochre, Plate 07/1, page 101.

*Flesh.*—*Color*—near Majolica Yellow, Plate 09/2, page 102, flecked with Currant Red, Plate 821/3, page 167. Surface of pit cavity—near Currant Red, Plate 821/3, page 167, varying somewhat; deeper depressions darker than shallow depressions. *Texture*—medium fine; melting. *Juice*—abundant; rich. *Fibres*—medium fine; tender; average number. Ripens—even. *Flavor*—mildly austere; acid; a well balanced flavor, distinct and rich. *Aroma*—not pronounced. *Eating quality*—best.

*Stone.*—Free. *Adherence to flesh*—when fruits are hard ripe, the stone parts from flesh freely; flesh adheres to stone only at base. In soft ripe fruit occasionally long fibre-like threads adhere to stone, particularly on ventral side. *Size*—medium; length, 1 to 1⅛ inches; breadth, ¾ to ⅞ inch; thickness, ⅝ to ⅞ inch. *Form*—obovate—cuneate; cuneate toward base. Base—nearly straight. Hilum—narrow; oblong. Apex—nearly obtuse. Sides—slightly unequal; curved on right side. Surface—irregularly furrowed toward apex; ridged toward apex; pitted from base to above center. Two broad deep furrows on either side of ventral valve running from base to apex, but somewhat deeper at base. Ridges—rounded toward base and apex. Pits—elongated. Ventral edge—medium thick, with wing toward base. Dorsal edge—medium narrow with no groove; no ridges. *Color of stone*—near Sayal Brown, Plate XXIX (Ridgway), with pits and grooves near Chrysanthemum Crimson, Plate 824/3, page 169. *Tendency to split*—none.

Use: Market; local; dessert; excellent for home use as a fresh fruit.

Keeping quality: Medium

Resistance to: Slightly susceptible to brown rot.

Shipping quality: Medium.

I claim:

A new and distinct variety of nectarine plant characterized as to novelty by the red coloring of the yellow flesh of the fruit particularly about the pit; the rich flavor of the fruit; the intense all-over red color of the crispy thin skin; the early blooming habit of the tree and showy character of the blooms due both to the large quantity and large size of the same; its great resistance to delayed dormancy and consequent heavy productivity in Southern California and in other peach growing sections with similar climate, substantially as shown and described.

HERBERT C. SWIM.